US009523124B2

(12) United States Patent
Narahara et al.

(10) Patent No.: US 9,523,124 B2
(45) Date of Patent: Dec. 20, 2016

(54) DEVICE FOR NUCLEIC ACID ANALYSIS AND NUCLEIC ACID ANALYZER

(75) Inventors: Masatoshi Narahara, Hitachinaka (JP); Taro Nakazawa, Hitachinaka (JP); Ryoji Inaba, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 246 days.

(21) Appl. No.: 13/996,638

(22) PCT Filed: Dec. 13, 2011

(86) PCT No.: PCT/JP2011/078738
§ 371 (c)(1),
(2), (4) Date: Jun. 21, 2013

(87) PCT Pub. No.: WO2012/086450
PCT Pub. Date: Jun. 28, 2012

(65) Prior Publication Data
US 2013/0296197 A1    Nov. 7, 2013

(30) Foreign Application Priority Data
Dec. 21, 2010   (JP) ................................. 2010-284855

(51) Int. Cl.
*C12Q 1/68* (2006.01)
*B01L 3/00* (2006.01)

(52) U.S. Cl.
CPC .... *C12Q 1/6869* (2013.01); *B01J 2219/00286* (2013.01); *B01J 2219/00608* (2013.01);
(Continued)

(58) Field of Classification Search
CPC .. C12Q 1/6869; B01L 3/5027; B01L 2200/12; B01L 2300/0636; B01L 2300/0877; B01L 2300/0887; B01J 2219/00286; B01J 2219/00608; B01J 2219/00612; B01J 2219/00637; B01J 2219/00648; B01J 2219/00659; B01J 2219/00722
(Continued)

(56) References Cited

U.S. PATENT DOCUMENTS 7,115,400 B1    10/2006 Adessi et al.
7,223,363 B2 *  5/2007 McNeely et al. ............. 422/417
(Continued)

FOREIGN PATENT DOCUMENTS

JP    2003-9859    1/2003
JP    2006-64599   3/2006
(Continued)

OTHER PUBLICATIONS

Das et al. (Applied Physics Letters, 2010, vol. 96, pp. 133703-1-133703-3).*
(Continued)

*Primary Examiner* — Jeremy C Flinders
(74) *Attorney, Agent, or Firm* — Baker Botts L.L.P.

(57) ABSTRACT

Sample nucleic acids are prevented from removing from a sample-immobilizing layer during a sequencing reaction. A reaction device for nucleic acid analysis is provided that enables high throughput analysis by increasing the number of nucleic acid samples that can be analyzed. The reaction device for nucleic acid analysis comprises a substrate, a sample-immobilizing layer on the substrate, nucleic acid samples or carriers having nucleic acid samples on their surfaces, which are immobilized on the sample-immobilizing layer, and a blocking layer that covers areas other than areas where the nucleic acid samples or the carriers are bound to the sample-immobilizing layer, wherein the immobilizing layer is formed of an inorganic oxide.

3 Claims, 7 Drawing Sheets

A

B (52) U.S. Cl.
CPC ............... *B01J 2219/00612* (2013.01); *B01J 2219/00637* (2013.01); *B01J 2219/00648* (2013.01); *B01J 2219/00659* (2013.01); *B01J 2219/00722* (2013.01); *B01L 3/5027* (2013.01); *B01L 2200/12* (2013.01); *B01L 2300/0636* (2013.01); *B01L 2300/0877* (2013.01); *B01L 2300/0887* (2013.01)

(58) Field of Classification Search
USPC .......................................................... 506/26
See application file for complete search history.

(56) References Cited

U.S. PATENT DOCUMENTS

| | | | |
|---|---|---|---|
| 2003/0027154 A1* | 2/2003 | Narahara et al. ................. | 435/6 |
| 2009/0062129 A1 | 3/2009 | McKernan et al. | |
| 2010/0233429 A1 | 9/2010 | Goshoo et al. | |

FOREIGN PATENT DOCUMENTS

| | | |
|---|---|---|
| JP | 2006-87974 | 4/2006 |
| WO | WO 2007/032236 A1 | 3/2007 |

OTHER PUBLICATIONS

Yao et al. (Analytical Biochemistry, 2006, vol. 354, pp. 220-228).*
Zhu et al. (Analytica Chimica Acta, 2004, vol. 510, pp. 163-168).*
Das et al. (Langmuir, 2009, vol. 25, pp. 235-241).*
Pulsipher et al. (J. Amer. Chem. Soc., 2009, 131:7626-7632).*
Hofer et al. (Langmuir, 2001, 17:4014-4020).*
Heise et al. (Top. Curr. Chem., 2006, 261:1-25).*
Fahrenkopf et al. (Mater. Res. Soc. Symp. Proc., Fall 2009, vol. 1236).*
Notice of Reasons for Rejection mailed Jun. 24, 2014, in connection with Japanese Application No. JP 2010-284855, 3 pages.
Notice of Allowance mailed Aug. 26, 2014, in connection with Japanese Application No. JP 2010-284855, 1 page.
International Preliminary Report on Patentability mailed Jun. 25, 2013, in connection with International Application No. PCT/JP2011/078738; 4 pages.
Ningning Zhu et al., Electrochemical detection of DNA hybridization using methylene blue and electro-deposited zirconia thin films on gold electrodes, Analytics Chimica Acta 510 (2004) 163-168.
Mandy Gnauck et al.., Carboxy-Terminated Oligo9ethylene glycol)-Alkane Phosphate: Synthesis and Self-Assembly on Titanium Oxide Surfaces, Langmuir 2007, 23, 377-381.
Marcel Margulies et al., Genome Sequencing in Open Microfabricated High Density Picoliter Reactors, Nature. Sep. 15, 2005, 437(7057): 376-380.
Jay Shendure et al., Accurate Multiplex Polony Sequencing of an Evolved Bacterial Genome, Science Sep. 9, 2005, pp. 1728-1732, vol. 309.
Timothy D. Harris, et al., Single-Molecule DNA Sequencing of a Viral Genome, Science, Apr. 4, 2008, pp. 106-109, vol. 320.
Jung-Hui Wang et al., Alumina-promoted mesoporous sulfated zirconia: A catlayst for *n*-butane isomerization, Applied Catalysis A: General 286 (2005) 128-136.
Toshishige M. Suzuki et al., Adsorption and removal of oxo-anions of arsenic and selenium on the zirconium (IV) loaded polymer resin functionalized with diethlenetriamine-$N,N,N',N'$-polyacetic acid, J. Environ. Monit., 2000, 2, 550-555.
Mark Schena et al., Parallel human genome analysis: Microarray-based expression monitoring of 1000 genes, Pro. Natl. Aca. Sci USA, Oct. 1996, pp. 10614-10619, vol. 93.

* cited by examiner

DEVICE FOR NUCLEIC ACID ANALYSIS AND NUCLEIC ACID ANALYZER

TECHNICAL FIELD

The present invention relates to a device for nucleic acid analysis and a nucleic acid analyzer.

BACKGROUND ART

Novel technology for determining the nucleotide sequence of DNA or RNA has been developed.

Today, with generally used methods that employ electrophoresis, a cDNA fragment sample synthesized in advance through reverse transcription reaction of a DNA fragment or an RNA sample for sequencing is prepared, electrophoresis is performed after conducting a dideoxy reaction by the well-known Sanger method, and the molecular weight separation/development pattern is determined and analyzed.

Meanwhile, in recent years, a method for determining the sequence information of many fragments in parallel by immobilizing many DNA fragments as samples on a substrate has been suggested. (Patent Documents 1 to 3 and Non-patent Documents 1 to 8).

Non-Patent Document 1 describes PCR performed on microparticles used as carriers carrying DNA fragments. After PCR, microparticles carrying PCR-amplified DNA fragments are introduced into many wells provided on a plate, which have diameters adjusted to the sizes of the microparticles, followed by pyrosequencing.

In addition, Non-Patent Document 2 describes PCR performed on microparticles used as carriers carrying DNA fragments. After PCR, microparticles are spread and immobilized on a glass substrate. An enzymatic reaction (ligation) is conducted on the glass substrate. Sequence information about each fragment is obtained by incorporating labeled nucleotides into the fragment and detecting fluorescence.

Further, Non-Patent Document 3 describes that many DNA probes having identical sequences are immobilized in advance on a substrate. In addition, after a DNA sample is sheared, a DNA probe sequence and an adapter sequence complementary to the DNA probe sequence are added to one end of each DNA fragment. These are hybridized on a substrate and thus sample DNA fragments are individually (one molecule by one molecule) immobilized at random on the substrate. In such case, a DNA extension reaction is conducted on the substrate to incorporate in advance labeled nucleotides, followed by washing of unreacted nucleotides and fluorescence detection. Thus, sequence information about each sample DNA is obtained.

As described above, methods for determining the sequence information of many fragments in parallel by immobilizing many nucleic acid fragment samples on a substrate have been developed. Such methods are being put into practical use.

Patent Document 1 discloses a method for immobilizing nucleic acid samples to a reaction device for nucleic acid analysis, which is used for a method for determining a lot of sequence information in parallel. The reaction device for nucleic acid analysis comprises a substrate having a sample-immobilizing layer and a spacer without a central part (the central part having been hollowed out) installed in a chamber, wherein the upper part of the chamber, the spacer, and the substrate are pressure-bonded by pressurization. A hollow part formed by the flat plate of the upper part of the chamber and the spacer and the flat plate part of the substrate form a flow channel. Injection and discharge of a solution is carried out via two tubes at the upper part of the chamber. The flat plate of the upper part of the chamber and the flat plate part of the substrate are always pressurized during use, thereby preventing leakage from the interface between the flat plate of the upper part of the chamber and the spacer, and the interface between the spacer and the flat plate part of the substrate.

The sample-immobilizing layer of Patent Document 1 improves the adhesive property between a nucleic acid sample and a substrate. A functional group is introduced into a nucleic acid sample, the functional group introduced into the nucleic acid sample interacts with a functional group of the sample-immobilizing layer, so as to improve the adhesive property. As a sample-immobilizing layer, organic material such as acrylamide, polylysine, streptavidin, or a silanized layer is used. A method using a silanized layer involves introducing a functional group such as an amino group, a carboxylic acid, or an aldehyde group into an immobilizing layer. Through the use of an arbitrary cross-linking reagent, a functional group introduced into a sample-immobilizing layer reacts with a functional group to be introduced into a nucleic acid sample, so as to immobilize the nucleic acid sample. As a functional group to be introduced into a nucleic acid sample, acrydite, biotin, amino groups, and the like are disclosed.

PRIOR ART DOCUMENTS

Patent Documents

Patent Document 1: Publication of U.S. Patent Application No. 2009/0062129
Patent Document 2: JP Patent Publication (Kokai) No. 2006-87974 A
Patent Document 3: U.S. Pat. No. 7,115,400B1

Non-Patent Documents

Non-patent Document 1: Nature 2005, vol. 437, pp. 376-380.
Non-patent Document 2: Science 2005, vol. 309, pp. 1728-1732
Non-patent Document 3: Science 2008, vol. 320, pp. 106-109.
Non-patent Document 4: Langmuir 2007, vol. 23, pp. 377-381
Non-patent Document 5: Analytica Chimica Acta Vol. 510, pp. 163-168
Non-patent Document 6: Applied Catalysis A: General. 2005, vol. 286, pp. 128-136
Non-patent Document 7: J. Environ. Monit. 2000, vol. 2, pp. 550-555
Non-patent Document 8: Proc. Natl. Acad. Sci. U.S.A. 1996, Vol. 93, pp. 10614-10619

SUMMARY OF THE INVENTION

Problems to be Solved by the Invention

The methods described in Patent Document 1 and Patent Document 2 above enable efficient analyses in that a reaction is conducted in a flow channel formed of the hollow part (formed of the flat plate of the upper part of the chamber and the spacer) and the flat part of the substrate.

In general, the deformation amount of a spacer depends on the film thickness of the spacer. When the film thickness is large, the deformation amount of the spacer is also high.

Moreover, the spacer will more easily fit the irregularity of the substrate, so that leakage does not occur easily. However, when the spacer is thinned, the amount of deformation due to pressurization decreases and the risk of leakage increases. Thus, there is a problem such that a spacer cannot be thinned. As described above, the reaction device of Patent Document 1 is problematic in that the spacer is thick and the capacity of a flow channel is large. In general, since reagents to be used for nucleic acid analysis are expensive, the nucleic acid analysis system of Patent Document 1 is problematic in that the amount of a reagent to be used is large and the running cost for analysis is high.

As a reaction device having a low-volume flow channel, Patent Document 2 discloses a reaction device in which a chamber, a spacer, and a substrate are integrated. As a spacer material, an epoxy resin or an acrylate resin, or polydimethylsiloxane is used. However, a temperature for processing the above spacer material and a temperature for bonding the spacer material with a sample layer are as high as 100° C. or higher, resulting in a problem such that an organic matter as a sample-immobilizing layer is damaged by heat. Furthermore, a problem occurs due to thermal damage such that a sample nucleic acid removes during DNA extension reaction.

Non-patent Document 4 and Non-patent Document 5 disclose methods using inorganic oxide (e.g., titania and zirconia) as a sample-immobilizing layer. Inorganic oxide is stable even at a temperature of 100° C. or higher. Accordingly, thermal damage upon processing of a spacer material and bonding with a sample-immobilizing layer can be prevented.

In general, it is known that a functional group containing oxygen is specifically adsorbed to an inorganic oxide. As such a functional group, Non-patent Document 5 discloses phosphoric acid, Non-patent Document 6 discloses sulfuric acid, and Non-patent Document 7 discloses acetic acid. Non-patent Document 5 discloses a method for immobilizing an oligonucleotide having phosphorylated ends on zirconia. However, adsorption of a functional group containing oxygen to an inorganic oxide is a reversible reaction and thus is problematic in that a substitution reaction with a hydroxide ion, a chloride ion, and a nitrate ion contained in an extension reaction solution proceeds and then nucleic acid samples remove.

An object of the present invention is to address the above problems of the conventional reaction devices for nucleic acid analysis and to provide a device and an apparatus whereby: the volume of a flow channel where a nucleic acid reaction takes place is small; a layer for immobilizing sample nucleic acids do not remove during device production; nucleic acid samples are prevented from removing from the substrate during a nucleic acid reaction; and nucleic acid analysis can be conducted efficiently at low cost.

Means for Solving the Problem

As a result of intensive studies, the inventors of the present invention have completed a reaction device for nucleic acid analysis, which has low flow channel volume, can be produced without removing from an immobilizing layer for immobilization of nucleic acid samples, and can conduct a nucleic acid reaction such as an extension reaction for DNA sequencing or the like without causing sample nucleic acids to remove.

The present invention relates to a reaction device for nucleic acid analysis comprising a substrate, a sample-immobilizing layer on the substrate, nucleic acid samples immobilized on the sample-immobilizing layer or carriers having nucleic acid samples on the surfaces, and a blocking layer that covers an area other than an area where the nucleic acid sample or the carrier is bound to the sample-immobilizing layer. The blocking layer prevents a reaction solution from infiltrating into the binding areas of nucleic acid samples binding to the sample-immobilizing layer, so as to be able to prevent the nucleic acid samples from removing from the sample-immobilizing layer.

The sample-immobilizing layer of the reaction device for nucleic acid analysis of the present invention is formed of an inorganic oxide. Such an inorganic oxide forming the sample-immobilizing layer is selected from the group consisting of titania, zirconia, alumina, zeolite, vanadium pentoxide, silica, sapphire, tungsten oxide, and tantalum pentoxide, and may be a mixture of at least 2 types thereof. Of these examples, titania, zirconia, alumina, zeolite, and vanadium pentoxide, or mixtures thereof are desired. The inorganic oxide binds to a phosphoric acid site or a phosphoric ester site within a nucleic acid sample molecule, so as to bind the nucleic acid sample to the sample-immobilizing layer. In particular, titania, zirconia, alumina, zeolite, and vanadium pentoxide contain many Lewis acid sites or Brønsted acid sites having high electrophilicity to which DNA can bind.

Furthermore, the blocking layer of the present invention is formed using a carboxylic compound, a phosphate compound, a sulfuric acid compound, a nitrile compound, a salt of any one of them, or a mixture of at least 2 types of these compounds. These compounds specifically bind to an inorganic oxide and realize a high blocking effect by which a reaction solution is prevented from infiltrating into the binding sites of nucleic acid samples binding to the sample-immobilizing layer.

Furthermore, the reaction device for nucleic acid analysis of the present invention has a solution inlet port and a solution outlet port, as well as a flow channel for flowing a solution. An inorganic oxide, by which no thermal damage, realizes processing of a spacer material at a high temperature and binding to the sample-immobilizing layer, and thus makes it possible to provide a reaction device, in which a chamber having a low flow channel volume, a spacer, and a substrate are integrated.

The reaction device for nucleic acid analysis of the present invention can be produced by immobilizing nucleic acid samples or carriers having nucleic acid samples on the surfaces on a substrate having a sample-immobilizing layer, and then introducing a blocking layer that covers areas other than areas where the nucleic acid samples or the carriers are bound to the sample-immobilizing layer. Blocking of areas other than areas where the nucleic acid samples or the carriers are bound to the sample-immobilizing layer is possible with a high coverage.

Moreover, the reaction device for nucleic acid analysis of the present invention can be produced by binding nucleic acid samples or carriers having nucleic acid samples on the substrate having the sample-immobilizing layer, simultaneously with introducing a blocking layer that covers areas other than areas where the nucleic acid samples or the carriers are bound to the sample-immobilizing layer. Immobilization of nucleic acid samples and a blocking layer can be realized at the same time, so that the time for producing the reaction device for nucleic acid analysis can be shortened.

Furthermore, an apparatus provided with the reaction device for nucleic acid analysis of the present invention, comprises the reaction device for nucleic acid analysis comprising a substrate, an immobilizing layer on the substrate, nucleic acid samples or carriers having nucleic acid samples on the surfaces, which are immobilized on the sample-immobilizing layer, and a blocking layer that covers areas other than areas where the nucleic acid samples or the carriers are bound to the sample-immobilizing layer; a means for injecting a solution that contains a reagent into the reaction device for nucleic acid analysis, a detection means for observation of samples retained in the reaction device for nucleic acid analysis, and the like. A number of nucleic acid samples can be simultaneously analyzed in parallel using the apparatus.

Specifically, the present invention is as follows.

[1] A reaction device for nucleic acid analysis, comprising
a substrate,
a sample-immobilizing layer on the substrate,
a nucleic acid sample or a carrier having a nucleic acid sample on its surface, which is immobilized on the sample-immobilizing layer, and
a blocking layer that covers an area other than an area where the nucleic acid sample or the carrier is bound to the sample-immobilizing layer, wherein the sample-immobilizing layer is formed of an inorganic oxide.

[2] The reaction device for nucleic acid analysis of [1], wherein the inorganic oxide is selected from the group consisting of titania, zirconia, alumina, zeolite, vanadium pentoxide, silica, sapphire, tungsten oxide, tantalum pentoxide, and a mixture of at least 2 types thereof.

[3] The reaction device for nucleic acid analysis of [2], wherein the inorganic oxide is selected from the group consisting of titania, zirconia, alumina, zeolite, vanadium pentoxide, and a mixture of at least 2 types thereof.

[4] The reaction device for nucleic acid analysis of any one of [1] to [3], wherein the blocking layer is selected from the group consisting of a carboxylic compound, a phosphate compound, a sulfuric acid compound, a nitrile compound, a salt thereof, and a mixture of at least 2 types of these compounds.

[5] The reaction device for nucleic acid analysis of [4], wherein the blocking layer is selected from the group consisting of a carboxylic compound, a sulfuric acid compound, a salt thereof, and a mixture of at least 2 types of these compounds.

[6] The reaction device for nucleic acid analysis of any one of [1] to [5], comprising:
a first substrate that comprises the sample-immobilizing layer, a nucleic acid sample or a carrier having a nucleic acid sample on its surface, which is immobilized on the sample-immobilizing layer, and a blocking layer that covers an area other than an area where the nucleic acid sample or the carrier is bound to the sample-immobilizing layer, wherein the sample-immobilizing layer is formed of an inorganic oxide;
a second substrate; and
a spacer having a hollow part for formation of a flow channel, wherein the first substrate and the second substrate are adhered to each other via the spacer to form the flow channel between the substrates,
within the flow channel, the sample-immobilizing layer, the nucleic acid sample or the carrier having the nucleic acid sample on its surface, which is immobilized on the immobilizing layer, and the blocking layer that covers an area other than an area where the nucleic acid sample or the carrier is bound to the sample-immobilizing layer are present, and
a solution inlet port and a solution outlet port that are in communication with the flow channel are provided.

[7] The reaction device for nucleic acid analysis of [6], wherein the spacer has a thickness of 1 mm or less.

[8] A method for producing a reaction device for nucleic acid analysis, comprising the steps of:
(i) forming a sample-immobilizing layer on a substrate;
(ii) immobilizing a nucleic acid sample or a carrier having a nucleic acid sample on its surface on the sample-immobilizing layer; and
(iii) introducing a blocking layer that covers an area other than an area where the nucleic acid sample or the carrier is bound to the sample-immobilizing layer, wherein
the sample-immobilizing layer is formed of an inorganic oxide.

[9] The method for producing a reaction device for nucleic acid analysis of [8], wherein the inorganic oxide is selected from the group consisting of titania, zirconia, alumina, zeolite, vanadium pentoxide, silica, sapphire, tungsten oxide, tantalum pentoxide, and a mixture of at least 2 types thereof.

[10] The method for producing a reaction device for nucleic acid analysis of [9], wherein the inorganic oxide is selected from the group consisting of titania, zirconia, alumina, zeolite, vanadium pentoxide, and a mixture of at least 2 types thereof.

[11] The method for producing a reaction device for nucleic acid analysis of any one of [8] to [10], wherein the blocking layer is selected from the group consisting of a carboxylic compound, a phosphate compound, a sulfuric acid compound, a nitrile compound, a salt thereof, and a mixture of at least 2 types of these compounds.

[12] The method for producing a reaction device for nucleic acid analysis of [11], wherein the blocking layer is selected from the group consisting of a carboxylic compound, a sulfuric acid compound, a salt thereof, and a mixture of at least 2 types of these compounds.

[13] The method for producing a reaction device for nucleic acid analysis of any one of [9] to [12], whereby
(ii) the step of immobilizing a nucleic acid sample or a carrier having a nucleic acid sample on its surface on the sample-immobilizing layer, and (iii) the step of introducing the blocking layer that covers an area other than an area where the nucleic acid sample or the carrier is bound to the sample-immobilizing layer are performed simultaneously.

[14] The method for producing a reaction device for nucleic acid analysis of [8], comprising the steps of:
(a) forming a sample-immobilizing layer on a first substrate;
(b) bonding the first substrate and a second substrate to each other via a spacer having a hollow part for formation of a flow channel;
(c) injecting a solution that contains a nucleic acid sample or a carrier having a nucleic acid sample on its surface from a solution inlet port that is in communication with the flow channel that opens into the first substrate, the spacer, or the second substrate, thereby immobilizing the nucleic acid sample or the carrier having the nucleic acid sample on its surface on the sample-immobilizing layer; and
(d) injecting a solution of a compound that can form the blocking layer from the solution inlet port, thereby introducing a blocking layer that covers an area other than an area where the nucleic acid sample or the carrier is bound to the sample-immobilizing layer, wherein the sample-immobilizing layer is formed of an inorganic oxide.

[15] A nucleic acid analyzer for nucleic acid analysis, comprising:
a reaction device for nucleic acid analysis that comprises at least a substrate, a sample-immobilizing layer on the substrate, a nucleic acid sample or a carrier having a nucleic acid sample on its surface, which is immobilized on the sample-immobilizing layer, and a blocking layer that covers an area other than an area where the nucleic acid sample or the carrier is bound to the sample-immobilizing layer, wherein the sample-immobilizing layer is formed of an inorganic oxide;

a reagent supply unit for supplying a solution that contains a reagent to the reaction device for nucleic acid analysis; and a detection unit for observation of a sample retained in the reaction device for nucleic acid analysis, wherein the sample-immobilizing layer is formed of an inorganic oxide.

[16] The nucleic acid analyzer of [15], wherein the inorganic oxide is selected from the group consisting of titania, zirconia, alumina, zeolite, vanadium pentoxide, silica, sapphire, tungsten oxide, tantalum pentoxide, and a mixture of at least 2 types thereof.

[17] The nucleic acid analyzer of [16], wherein the inorganic oxide is selected from the group consisting of titania, zirconia, alumina, zeolite, vanadium pentoxide, and a mixture of at least 2 types thereof.

[18] The nucleic acid analyzer of any one of [15] to [17], wherein the blocking layer is selected from the group consisting of a carboxylic compound, a phosphate compound, a sulfuric acid compound, a nitrile compound, a salt thereof, and a mixture of at least 2 types of these compounds.

[19] The nucleic acid analyzer of [18], wherein the blocking layer is selected from the group consisting of a carboxylic compound, a sulfuric acid compound, a salt thereof, and a mixture of at least 2 types of these compounds.

[20] The nucleic acid analyzer of any one of [15] to [19], wherein the reaction device for nucleic acid analysis comprises:

a first substrate that comprises a sample-immobilizing layer, a nucleic acid sample or a carrier having a nucleic acid sample on its surface, which is immobilized on the sample-immobilizing layer, and a blocking layer that covers an area other than an area where the nucleic acid sample or the carrier is bound to the sample-immobilizing layer, wherein the sample-immobilizing layer is formed of an inorganic oxide;

a second substrate; and a spacer having a hollow part for formation of a flow channel, wherein the first substrate and the second substrate are adhered to each other via the spacer to form the flow channel between the substrates, within the flow channel, the sample-immobilizing layer, the nucleic acid sample or the carrier having the nucleic acid sample on its surface, which is immobilized on the sample-immobilizing layer, and the blocking layer that covers an area other than an area where the nucleic acid sample or the carrier is bound to the sample-immobilizing layer, are present, and a solution inlet port and a solution outlet port that are in communication with the flow channel are provided.

This description includes part or all of the content as disclosed in the description and/or drawings of Japanese Patent Application No. 2010-284855, which is a priority document of the present application.

Effects of the Invention

According to the present invention, a reaction device for nucleic acid analysis in which the capacity of a flow channel is low and a nucleic acid reaction can be conducted without causing nucleic acid samples to become detached can be provided. The reaction device for nucleic acid analysis has a low-capacity flow channel(s) in which a reaction is conducted, so that the amount of the reagent to be used can be decreased and a large number of samples can be analyzed at low cost with high throughput. Furthermore, nucleic acid samples do not easily become detached from the sample-immobilizing layer during reactions, so that precise and efficient analyses can be conducted. Moreover, an inorganic oxide causing no thermal damage is used for the sample-immobilizing layer for immobilization of nucleic acid samples. Hence, even if the adhesion of a substrate on which the sample-immobilizing layer has been formed is performed upon production at a high temperature, the immobilizing layer is not degraded and the device can be produced at a higher yield rate.

EMBODIMENTS FOR CARRYING OUT THE INVENTION

Hereinafter, the above and other novel features and the effects of the present invention are described with reference to the drawings.

Here, in order to help complete understanding of the present invention, specific embodiments of the present invention are described in detail. However, the present invention is not limited to the content described herein. Furthermore, Examples can be appropriately combined and the combined forms thereof are also disclosed in the Description.

Example 1

Figure 1:
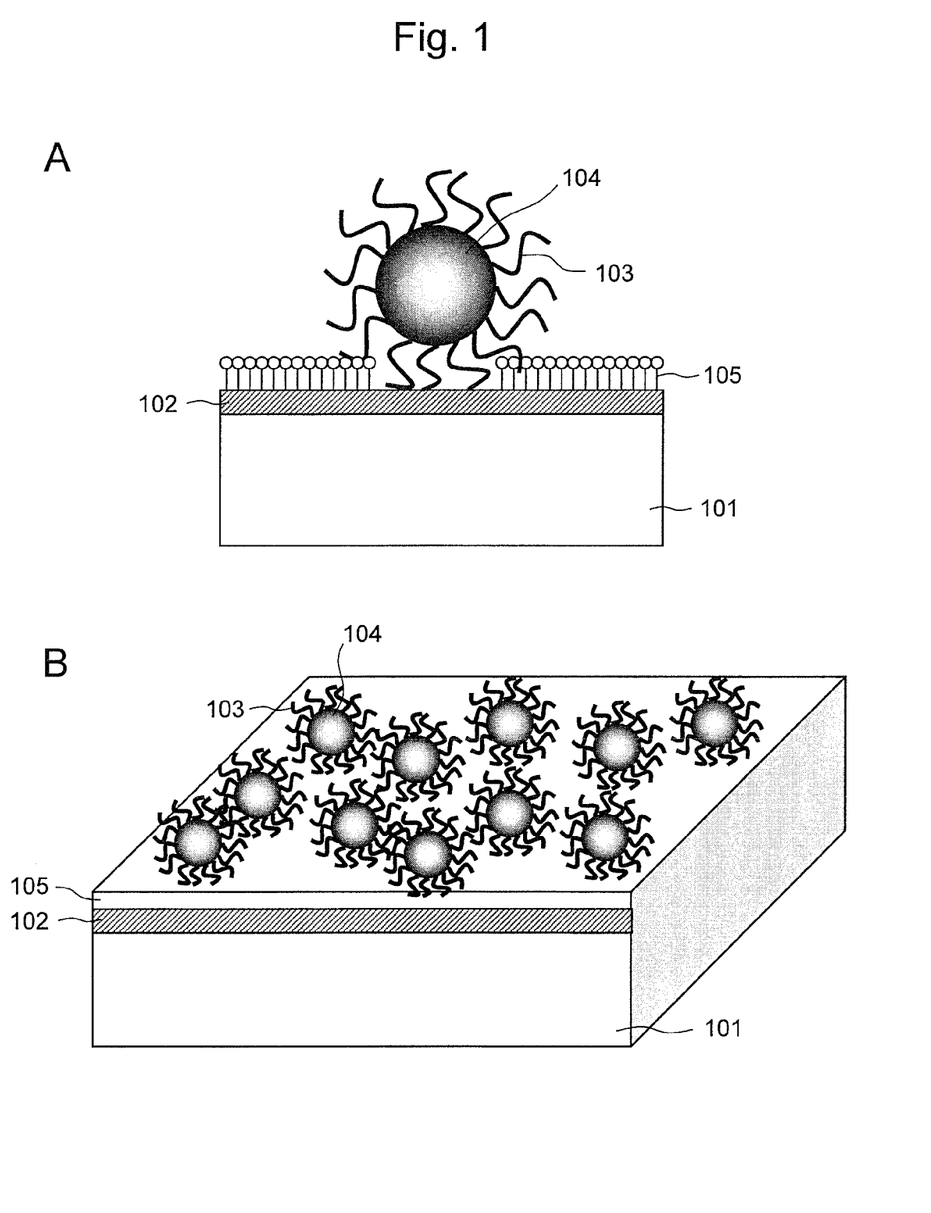
FIG. 1 is a diagram for explaining an example of the configuration of the reaction device for nucleic acid analysis of the present invention.

FIG. 1 shows an example of the reaction device for nucleic acid analysis of the present invention.

FIG. 1B shows a condition in which a sample-immobilizing layer 102 is laminated on a substrate 101 of the reaction device for nucleic acid analysis and carriers 104 containing nucleic acid samples 103 have been bound to the sample-immobilizing layer 102. FIG. 1A shows a side view of a condition in which a carrier 104 having nucleic acid samples 103 on the surface has been bound to the sample-immobilizing layer 102 via the nucleic acid samples 103. A blocking layer 105 is formed so as to cover areas other than the areas at which the nucleic acid samples are bound to the sample-immobilizing layer.

The sample-immobilizing layer 102 is layered on the substrate 101 and carriers 104 containing nucleic acid samples 103 are immobilized on the sample-immobilizing layer 102 via the nucleic acid samples 103. Many nucleic acid samples 103 are bound to the carriers 104. Specifically, some nucleic acid samples bind to carriers with one end thereof binding to the carrier and the other end thereof binding to the sample-immobilizing layer 102, while nucleic acid samples other than those binding to the sample-immobilizing layer bind to the sample-immobilizing layer 102 with only one end binding to the sample-immobilizing layer 102. When analysis is conducted using the reaction device for nucleic acid analysis of the present invention, nucleic acids binding to the carriers 104 react. On the sample-immobilizing layer 102, areas other than the binding area of nucleic acid samples 103 are covered by the blocking layer 105.

The substrate 101 to be used herein is made of a resin that fluorescence can transmit completely, such as glass, acrylate resin, or cyclo olefin polymer.

The blocking layer is formed by immobilizing a compound for blocking on the sample-immobilizing layer. The blocking layer blocks areas other than the areas at which nucleic acid samples are bound to the sample-immobilizing layer, so that it can prevent a reaction solution from infiltrating with the binding parts between the nucleic acid samples 103 and the sample-immobilizing layer 102. Moreover, this can prevent the nucleic acid samples 103 from becoming detached from the sample-immobilizing layer 102.

As the sample-immobilizing layer 102, an inorganic oxide to which a functional group containing oxygen is specifically adsorbed as is known, is used. In particular, a compound having Lewis acid sites or Brønsted acid sites on the surface is desired. Such an inorganic oxide is selected from the group consisting of titania, zirconia, alumina, zeolite, vanadium pentoxide, silica, sapphire, tungsten oxide, and tantalum pentoxide, or may be a mixture of at least 2 types thereof. In particular, a compound having a high density of Lewis acid sites or Brønsted acid sites on the surface, such as the one selected from titania, zirconia, alumina, zeolite, and vanadium pentoxide is desired. To increase the binding strength with nucleic acids, positively charged dopants may be added by doping to these metal oxides. Moreover, these dopants may be coordinated on the surfaces. Examples of such dopants include magnesium ion, iron ion, zinc ion, calcium ion, lithium ion, nickel ion, cobalt ion, copper ion, aluminium ion, and manganese ion. Inorganic oxides are not easily denatured by heat and will never be denatured when the reaction device for nucleic acid analysis of the present invention is produced and processed using heat. The thickness of the sample-immobilizing layer 102 is not particularly limited. For fluorescence observation, the thickness thereof that increases the penetration at an excitation light wavelength is desired, such as 500 nm or less.

The carriers 104 containing the nucleic acid samples 103 can be prepared using emulsion PCR as described in Science 2005, vol. 309, pp. 1728-1732 (Non-patent Document 2). "Emulsion PCR" refers to a method that involves immobilizing one molecule of nucleic acid on a microparticle, performing PCR under conditions where a water drop existing in oil contains one microparticle in which one molecule of nucleic acid is immobilized, and thus amplifying the nucleic acid on the microparticle. To improve the adhesion between the nucleic acid samples 103 and the sample-immobilizing layer 102, functional groups may be introduced into the ends of nucleic acid samples using a ligation reaction. Examples of such a functional group include phosphoric acid and carboxylic acid.

As the carriers 104, microparticles, and particularly magnetic microparticles (magnetic beads) are desirably used, but examples thereof are not particularly limited thereto. In the above method for preparing samples using ligation, many processes for washing intermediates are present. At this time, the use of magnetic microparticles is desired since magnetic microparticles having nucleic acid samples on the surfaces can be easily recovered with a high sample recovery using magnetism. As magnetic microparticles, microparticles produced by granulating a magnetic material, microparticles produced by coating the surfaces with macromolecular substances such as agarose, dextran, polystyrene, and acrylamide with the use of magnetic materials as nuclei, and the like can be used. As magnetic microparticles, commercially available magnetic microparticles can be used, such as Dynabeads and Dynabeads Myone (Trademark) (Dynal). The particle diameters of magnetic microparticles range from 0.1 to 10 μm, and preferably range from 0.5 μm to 5 μm. With the use of the above emulsion PCR, multiple copies of amplified sample nucleic acids can bind to the magnetic microparticles. $10^3$ to $10^{30}$ nucleic acid molecules, and preferably $10^6$ to $10^{21}$ nucleic acid molecules may be bound per magnetic microparticle.

The blocking layer 105 is formed using a Lewis base compound such as a carboxylic compound, a phosphate compound, a sulfuric acid compound, a nitrile compound, or a salt thereof. A mixture of at least 2 types of these compounds may also be used herein. These Lewis base compounds specifically adsorb to the sample-immobilizing layer 102 comprises an inorganic oxide. As such a Lewis base compound, a compound having a hydrophobic site such as long chain alkyl within the molecule is desired, since the hydrophobic site prevents a reaction solution from entering the binding site. Examples of a carboxylic compound that can be used for formation of the blocking layer include sodium iminodiacetate ethylenediamine tetraacetate, ethylenediamine tetraacetate, ethylene glycol-bis(2-aminoethylether)-N,N,N',N'-tetraacetate, 10-carboxy-1-decanethiol, 7-carboxy-1-heptanethiol, 5-carboxy-1-pentanethiol, 10-carboxyl disulfide, 7-carboxyl heptyl disulfide, 5-carboxyl pentylsulfide, 15-carboxyl-1-pentadecanethiol, carboxy-EG6-undecanethiol, carboxy-EG6-hexadecanethiol, butyl formate, citronellyl formate, ethyl formate, formic acid geranyl undecanoate, and a salt thereof. Examples of a phosphate compound include glyceraldehyde sphingosine 3-phosphate, 1-phosphoric acid 1-deoxy-D-xylulose-5-phosphate, 3-sn-phosphatidic acid, O-phosphoryl ethanolamine 2-aminoethyl dihydrogenphosphate, and a salt thereof. Examples of a sulfuric acid compound include sodium decyl sulfate, sodium dodecyl sulfate, and sodium octyl sulfate. Also, examples of a nitrile compound include dicyanopentane, dicyanohexane, (butylamino)acetonitrile, (dimethylamino)propionitrile, and hexynenitrile.

Figure 2:
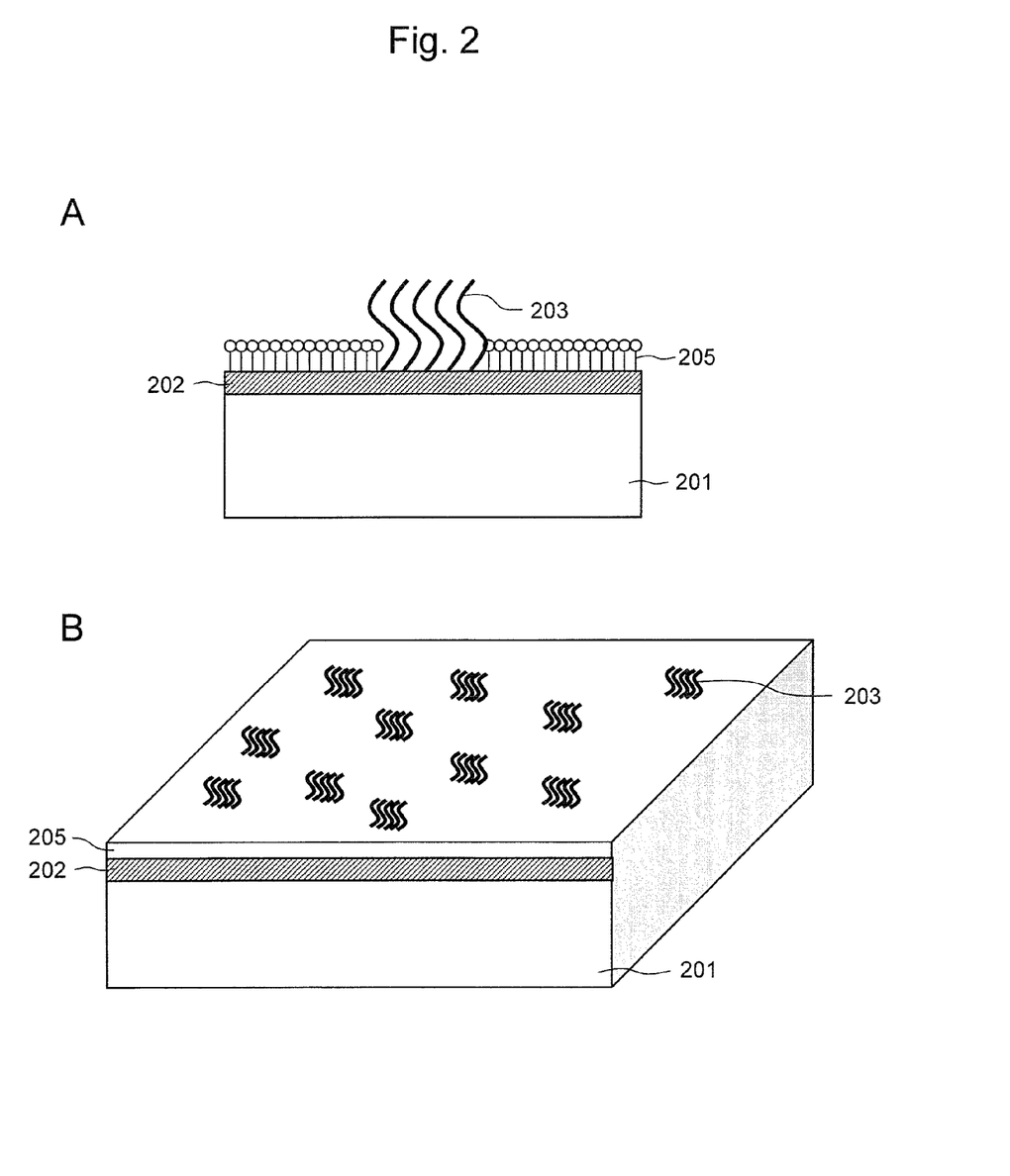
FIG. 2 is a diagram for explaining an example of the configuration of the reaction device for nucleic acid analysis of the present invention.

Another embodiment of the present invention is explained using FIG. 2. FIG. 2B shows a condition in which a sample-immobilizing layer 202 is laminated on a substrate 201 of a reaction device for nucleic acid analysis and nucleic acid samples 203 have been bound to the sample-immobilizing layer 202. FIG. 2A is a side view of a condition in which the nucleic acid samples 203 have been bound to the sample-immobilizing layer 202. A blocking layer 205 is formed so as to cover areas other than the areas at which nucleic acid samples are bound. A difference of this device with the reaction device for nucleic acid analysis shown in FIG. 1 is that no carrier 104 is used. Free nucleic acid samples 203 not bound to carriers are immobilized on the sample-immobilizing layer. An amplification reaction is conducted on the substrate according to the method described in U.S. Pat. No. 7,115,400B1 (Patent Document 3), nucleic acid samples 203 can be immobilized at arbitrary positions on the sample-immobilizing layer 202 formed on the substrate 201. Furthermore, nucleic acid samples 203 can also be immobilized using the spotting method described in Proc. Natl. Acad. Sci. U.S.A. 1996, Vol. 93, pp. 10614-10619 (Non-patent Document 8). Through forming of the blocking layer 205 after immobilization of nucleic acid samples 203, the reaction device for nucleic acid analysis of the present invention can be produced. The substrate, the sample-immobilizing layer, and the blocking layer to be used herein are similar to those for the reaction device for nucleic acid analysis shown in FIG. 1.

Figure 3:
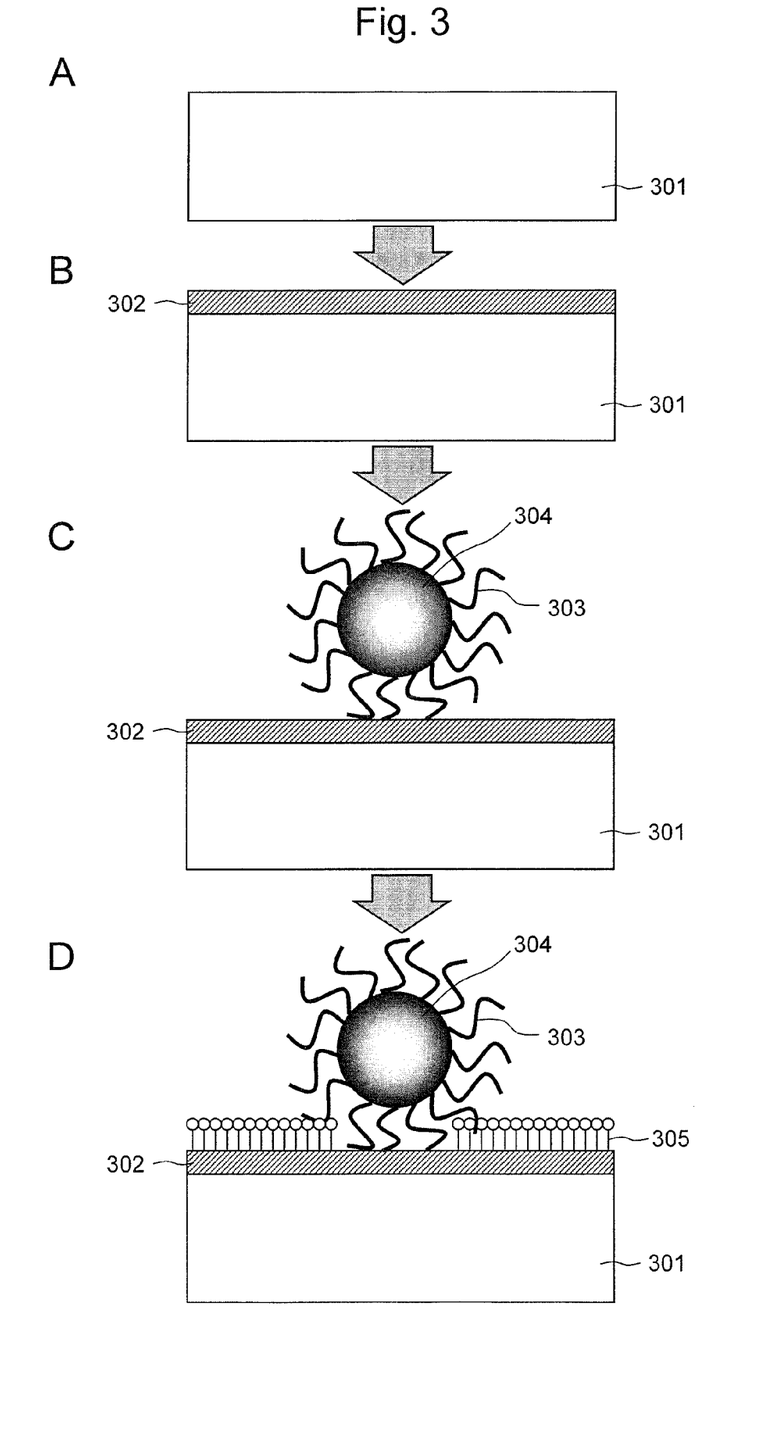
FIG. 3 is a diagram for explaining an example of the method for producing the reaction device for nucleic acid analysis of the present invention.

Next, a method for producing the reaction device for nucleic acid analysis of the present invention is explained using FIG. 3. An inorganic oxide film is formed on a substrate 301 (FIG. 3A) so as to form the film of a sample-immobilizing layer 302 (FIG. 3B). A film formation method that can be employed herein is not particularly limited and is sputtering or vapour deposition, with which thin films can be formed to have almost uniform film thicknesses. An aqueous solution containing a carrier 304 that has nucleic acid samples 303 on the surface is retained on the sample-immobilizing layer 302 for a period of time, so that nucleic acid samples 303 are immobilized (FIG. 3C). Immobilization conditions are not limited. For example, an aqueous solution containing the carrier 304 is retained at 4° C. to 80° C. for 1 second to 24 hours. The carrier density in the aqueous solution containing the carrier 304 at this time may be appropriately determined depending on the purpose or the like of nucleic acid analysis, such as $10^3$ to $10^6$ carriers/μL. An immobilization reaction of nucleic acid samples 303 to the inorganic oxide competes with a coordination reaction of a hydroxide ion within the aqueous solution. To increase the immobilization rate of nucleic acid samples 303, the immobilization reaction is desirably conducted under acidic conditions by which the concentration of a hydroxide ion within the aqueous solution can be decreased, that is, pH1 to 7, and preferably pH3 to 7. At this time, the carrier 304 having nucleic acid samples 303 on its surface is bound with a high degree of density to the sample-immobilizing layer 302 via the nucleic acid samples. The density of the carriers to be bound at this time may be appropriately determined depending on the purpose or the like of nucleic acid analysis. For example, the density ranges from $10^2$ to $10^6$ carriers and preferably ranges from $10^4$ to $10^6$ carriers per $cm^2$ of the sample-immobilizing layer. The number of molecules of nucleic acid samples to be bound per $cm^2$ of the sample-immobilizing layer ranges from $10^6$ to $10^{180}$ molecules, and preferably ranges from $10^{10}$ to $10^{150}$ molecules.

Subsequently, a blocking layer is formed on areas other than the binding areas of the carrier 304 binding via the nucleic acid samples 303 to the sample-immobilizing layer (FIG. 3D). The blocking layer is formed by retaining a solution of a compound to be used for formation of the blocking layer on the sample-immobilizing layer for a period of time. Conditions for formation of the blocking layer are not limited. For example, a compound to be used for the formation of the blocking layer may be retained at 20° C. to 80° C. for 1 second to 24 hours.

Figure 4:
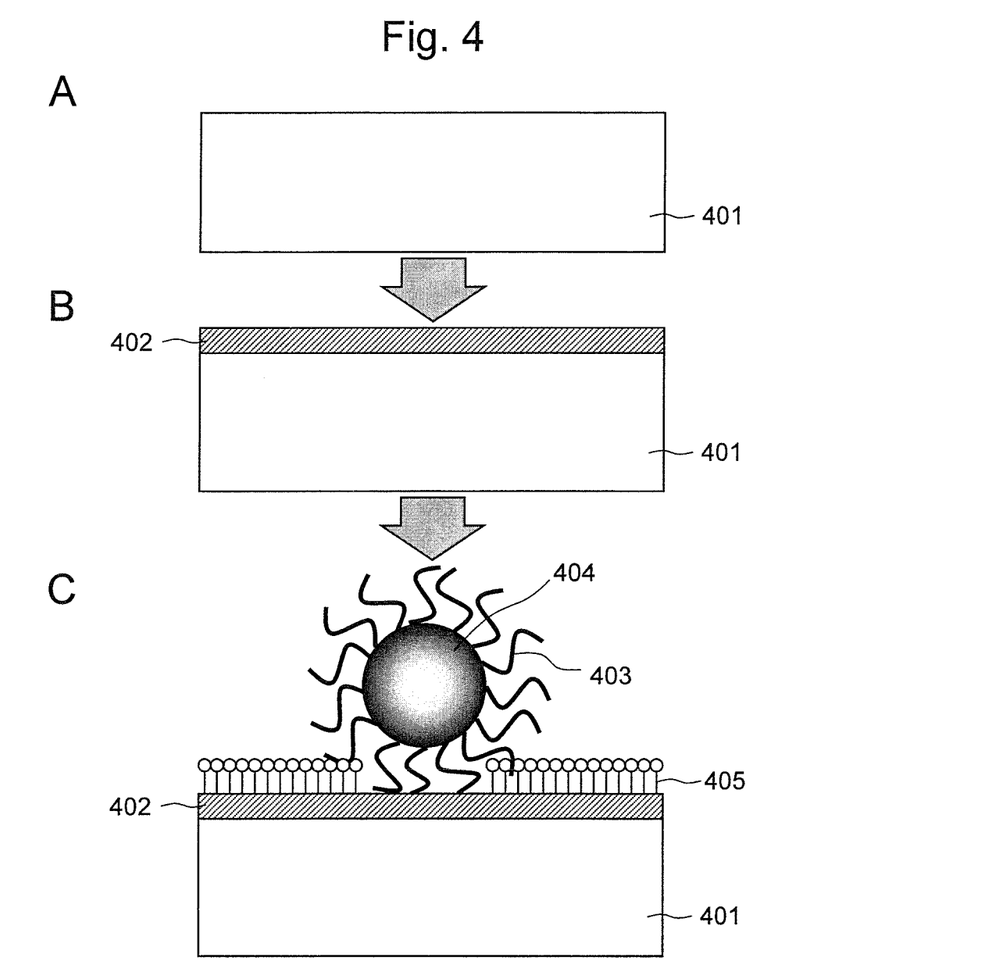
FIG. 4 is a diagram for explaining an example of the method for producing the reaction device for nucleic acid analysis of the present invention.

Another method for producing the reaction device for nucleic acid analysis of the present invention is explained using FIG. 4. A difference of this method with the production method shown in FIG. 3 is that immobilization of nucleic acid samples 403 and forming of a blocking layer 405 are performed simultaneously. An aqueous solution containing both a carrier 404 having nucleic acid samples 403 on its surface and a compound for formation of a blocking layer 405 is retained on a sample-immobilizing layer 402 for a period of time, thereby performing immobilization of the nucleic acid samples 403 and the formation of the blocking layer 405 simultaneously (FIG. 4C). Conditions for binding the carrier 404 and the conditions for formation of the blocking layer are similar to those described above.

The above FIG. 3 and FIG. 4 show cases in which nucleic acid samples are bound to the surfaces of carriers and then the carriers are bound to a sample-immobilizing layer. As in the case of the reaction device for nucleic acid analysis shown in FIG. 2, free nucleic acid samples not to be bound to any carrier may be bound to a sample-immobilizing layer. In this case, the number of molecules of nucleic acid samples to be bound per $cm^2$ of the sample-immobilizing layer ranges from $10^6$ to $10^{180}$ molecules and preferably ranges from $10^{10}$ to $10^{150}$ molecules.

Figure 5:
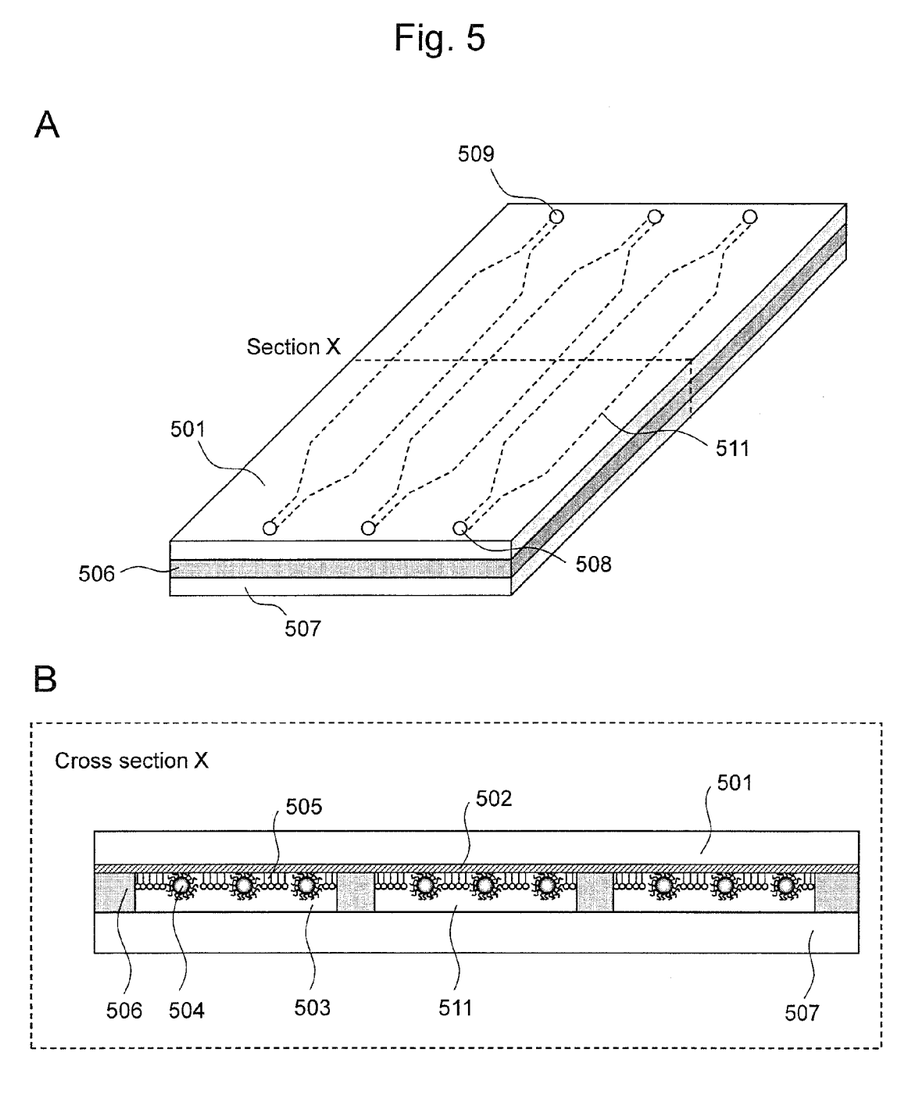
FIG. 5 is a diagram for explaining an example of the configuration of the reaction device for nucleic acid analysis of the present invention.

Another embodiment of the present invention is explained using FIG. 5. The reaction device for nucleic acid analysis shown in FIG. 5 is a device produced to contain the reaction device for nucleic acid analysis illustrated in FIG. 1 and FIG. 2 within flow channels. FIG. 5A shows the overview of the reaction device for nucleic acid analysis. FIG. 5B is a cross-sectional view of section X in FIG. 5A. The reaction device for nucleic acid analysis in FIG. 5 is an integrated reaction device having solution inlet ports 508, solution outlet ports 509, and flow channels 511 for sending solution. Here, the term "integrated reaction device" refers to a device in which necessary components other than a reagent solution to be used for a reaction are formed in an integrated manner, and thus necessary reagents are supplied to the flow channels of the reaction device so that a series of reaction can be conducted. The reaction device for nucleic acid analysis is designed so that carriers 504 having nucleic acid samples 503 on their surfaces or free nucleic acid samples are contained within the flow channels. The reaction device comprises a sample-immobilizing layer 502 formed therein and a second substrate 507 in addition to a substrate 501 to which the carriers 504 having nucleic acid samples 503 on their surfaces or free nucleic acid samples are bound. In the reaction device for nucleic acid analysis shown in FIG. 5, a substrate on which the sample-immobilizing layer 502 is formed and to which the carriers 504 having the nucleic acid samples 503 on their surfaces or free nucleic acid samples are bound is referred to as "a first substrate." Flow channels 511 are each formed between the first substrate 501 and the second substrate 507. The flow channels function to supply a reagent required for a reaction for nucleic acid analysis, and also function as reaction chambers where reactions take place. Furthermore, to ensure the space for the flow channels, a spacer 506 is provided between the first substrate 501 and the second substrate 507. Specifically, the reaction device for nucleic acid analysis in FIG. 5 has a structure in which the substrate (first substrate) 501, the spacer 506 with hollow portions (partially hollowed out), and the second substrate 507 are pasted together. The flow channels 511 are formed with the substrate 501, the spacer hollow parts, and the second substrate 507. Reaction solutions are injected from solution inlet ports 508, and discharged from solution outlet ports 509. The openings of the solution inlet ports 508 and the solution outlet ports 509 are in communication with the flow channels of the reaction device for nucleic acid analysis. The openings may be on the top face or side faces of the first substrate. The openings of the inlet ports 508 and the solution outlet ports 509 may be on the spacer 506 or the second substrate 507. The material of the second substrate 507 is not particularly limited. When the second substrate 507 is used for a nucleic acid analyzer that comes into contact with a thermoregulation element, examples of a material for the second substrate 507 include inorganic materials such as silicon, glass, sapphire, and quartz, metal materials such as SUS, copper, and aluminium, and high heat conductive resin materials incorporating carbon fiber or inorganic filler. The thickness of the second substrate 507 is also not particularly limited, but is desirably 10 mm or less in order to increase heat conductivity.

The material of the spacer 506 is not particularly limited, and a thermosetting or photosetting epoxy adhesive, acryl adhesive, or the like as described in JP Patent Publication (Kokai) No. 2006-87974 A (Patent Document 2) can be used, for example. Moreover, an acrylate resin-based double-stick tape or the like can be used, for example. Examples of more preferable materials include glass, quartz, and sapphire, and polydimethylsiloxane having high adhesive strength with a transparent resin. The thickness of the spacer is not particularly limited. The thinner the thickness, the more reduced capacity of a flow channel. Thus, the amount of a reagent to be used herein can be decreased. The spacer 506 has desirably a thickness of 1 mm or less.

The nucleic acid analysis device shown in FIG. 5 may also be referred to as an integrated reaction device for nucleic acid analysis or a flow chip. The integrated reaction device for nucleic acid analysis shown in FIG. 1 or FIG. 2 can also be said to be the integrated reaction device for nucleic acid analysis shown in FIG. 5 or a part of a flow chip.

FIG. 5 shows an example of a device in which three flow channels are formed. However, the number of flow channels is not limited and may range from 1 to 1000, 1 to 100, or 1 to 10, for example. When the number of flow channels is high, many reactions can be conducted simultaneously, and thus it can be used as a device capable of conducting high throughput analyses.

Figure 6:
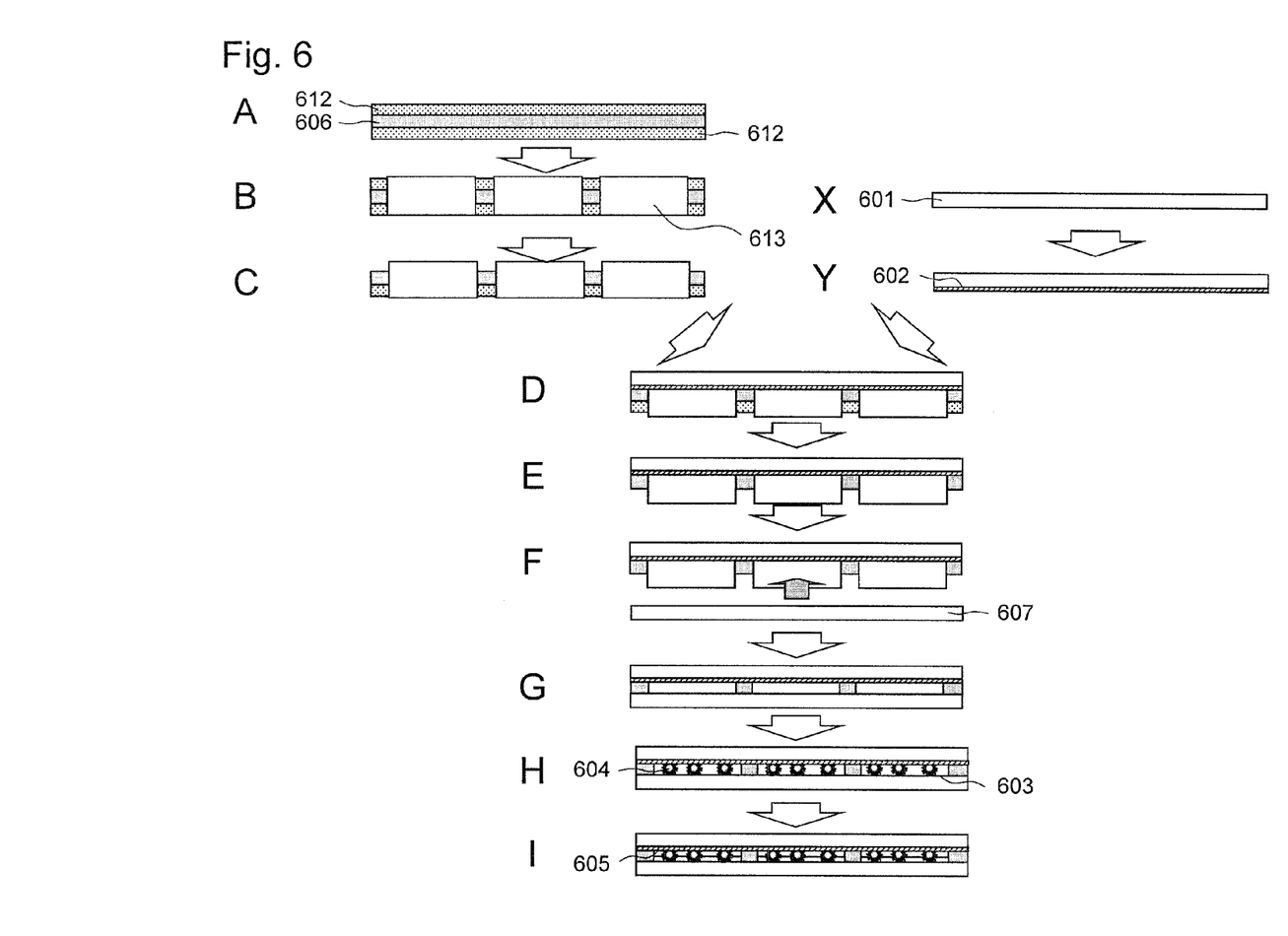
FIG. 6 is a diagram for explaining an example of the method for producing the reaction device for nucleic acid analysis of the present invention.

An example of a method for producing the integrated reaction device of the present invention shown in FIG. 5 is explained using FIG. 6. A spacer 606 (FIG. 6A) having mold films 612 on both surfaces thereof is hollowed out by press processing for pattern drawing, laser processing, or the like, so as to form hollow parts 613 corresponding to flow channel parts (FIG. 6B). After the mold film 612 on one surface is stripped off (FIG. 6C), a substrate 601 having a sample-immobilizing layer 602 (FIG. 6X and FIG. 6Y) and a spacer 606 are pasted together (FIG. 6D). To enhance the strength of the adhesion between the sample-immobilizing layer 602 and the spacer 606, the surface of the sample-immobilizing layer 602 and the surface of the spacer 606 may be subjected to excimer processing, oxygen plasma treatment, or atmospheric plasma treatment immediately before pasting. Moreover, heat treatment may be performed after pasting so as to enhance the adhesion between the two. Next, after removal of the remaining mold film 612 (FIG. 6E), similar treatment is performed to paste a second substrate to the resultant (FIG. 6F). After injection of an aqueous solution containing carriers 604 having nucleic acid samples 603 on the surfaces or free nucleic acid samples via the solution inlet ports 508 (FIG. 5), the solution is retained for a period of time to immobilize the nucleic acid samples 603 on the sample-immobilizing layer 602 (FIG. 6H). At this time, the carriers 604 having the nucleic acid samples 603 on their surfaces or free nucleic acid samples are immobilized almost uniformly on the sample-immobilizing layer. Thereafter, an aqueous solution of a compound selected from the group consisting of a carboxylic compound, a phosphate compound, a sulfuric acid compound, a nitrile compound, a salt thereof, and a mixture of at least two types of these compounds is similarly injected to form a blocking layer 605 (FIG. 6I).

The thus produced reaction device for nucleic acid analysis is installed in a nucleic acid analyzer and then nucleic acid analysis is conducted. The present invention also encompasses a nucleic acid analyzer for nucleic acid analysis, in which the reaction device for nucleic acid analysis of the present invention is installed. The nucleic acid analyzer of the present invention comprises at least the reaction device for nucleic acid analysis of the present invention, a means for injecting a solution containing a reagent into the reaction device for nucleic acid analysis, and a detection means for observation of a sample retained in the reaction device for nucleic acid analysis. Furthermore, the nucleic acid analyzer comprises at least the reaction device for nucleic acid analysis of the present invention, a holder unit for holding the device, a stage unit for transferring the device and the holder unit, a reagent supply unit for supplying a reagent, and a detection unit for observation of a sample. The reagent supply unit for supplying a reagent comprises a reagent container, a solution delivering unit, a nozzle, and a nozzle transport unit, as described below.

Figure 7:
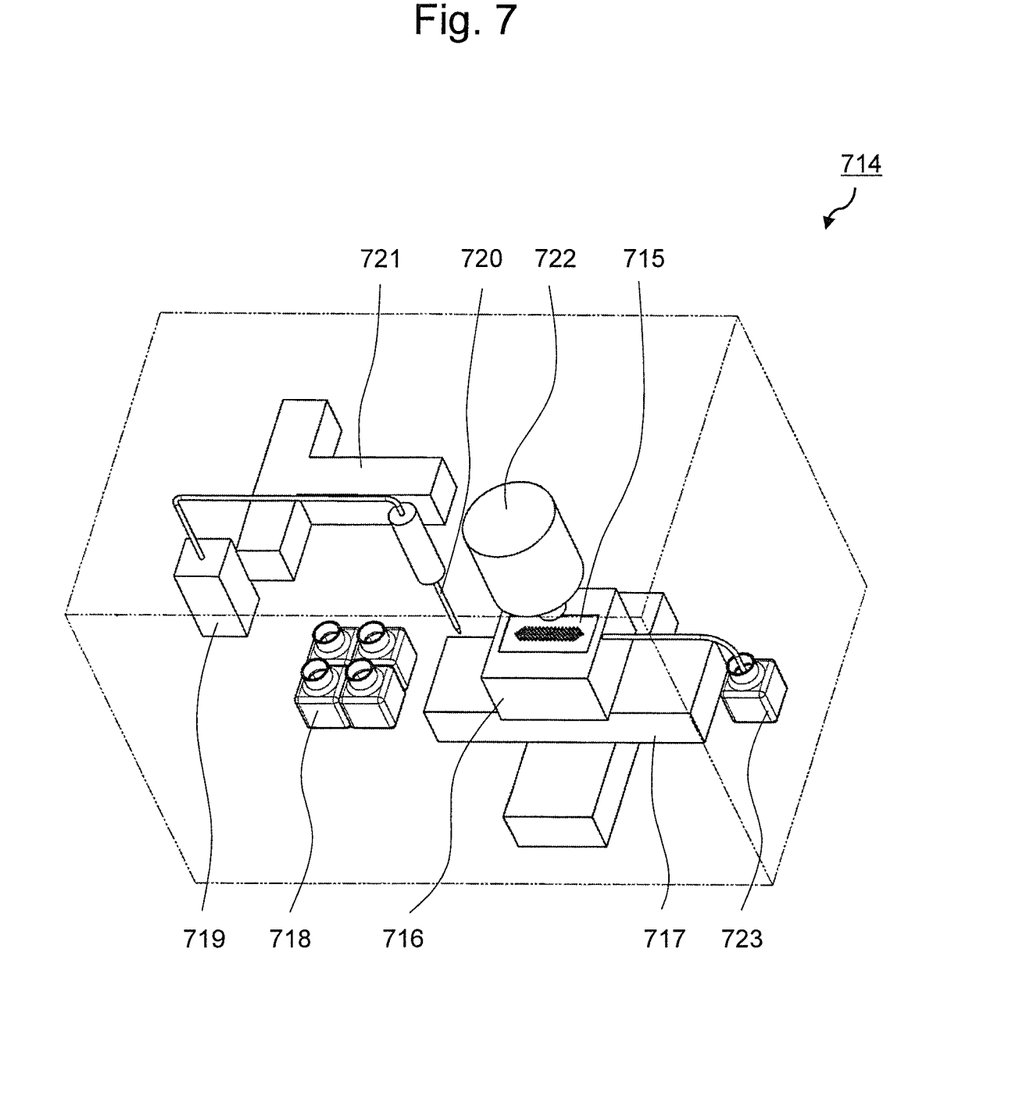
FIG. 7 is a diagram for explaining an example of the nucleic acid analyzer of the present invention.

An example of the nucleic acid analyzer of the present invention is explained using FIG. 7. A nucleic acid analyzer 714 comprises: the reaction device 715 for nucleic acid analysis of the present invention; a holder unit 716 that holds the reaction device 715 for nucleic acid analysis and can regulate the temperature of the reaction device 715 for nucleic acid analysis; a stage unit 717 for transferring the reaction device 715 for nucleic acid analysis and the holder unit 716; reagent containers 718 containing a plurality of reagents and wash water; a solution delivering unit 719 for aspirating reagents contained in the reagent container 718 and then injecting them into the reaction device 715 for nucleic acid analysis; a nozzle 720 for actually accessing the reagent containers 718 or the reaction device 715 for nucleic acid analysis upon reagent aspiration and/or discharge; a nozzle transport unit 721 for transporting the nozzle 720; a detection unit 722 for observation of samples immobilized in the reaction device 715 for nucleic acid analysis; and a waste solution container 723 for containing a waste solution, for example. The detection unit comprises a fluorescence detector, for example, whereby the reaction device for nucleic acid analysis on a stage unit can be irradiated with excitation light and then the thus generated fluorescence can be detected.

The nucleic acid analyzer of the present invention operates as described below. First, the reaction device 715 for nucleic acid analysis retaining a target nucleic acid sample is installed in the holder unit 716. Next, the nozzle 720 accesses the reagent container 718, to aspirate a reagent with the solution delivering unit 719. The nozzle 720 is transported to the top face of the reaction device 715 for nucleic acid analysis by the nozzle transport unit 721, so as to inject a reagent into the reaction device 715 for nucleic acid analysis. Subsequently, in the holder unit 716, thermoregulation is performed for nucleic acid samples and the reagent contained in flow channels of the reaction device 715 for nucleic acid analysis, so that a reaction takes place. For observation of the nucleic acid samples that have reacted, the reaction device 715 for nucleic acid analysis is transferred by the stage unit 717 and then exposed to excitation light, so that fluorescence from a plurality of nucleic acid samples within the detection regions is detected. At this time, preferably, excitation light is applied via the substrate on the side upon which nucleic acid samples or carriers having nucleic acid samples on their surfaces have been immobilized, and then fluorescence is detected. After detection, the reaction device 715 for nucleic acid analysis is slightly moved and detection is performed in a manner similar to that described above. This procedure is repeated multiple times. When observation of all detection regions is completed, wash water contained in the reagent container 718 is aspirated by the solution delivering unit 719 and then injected into the reaction device 715 for nucleic acid analysis, thereby washing the interior of the flow channel(s) within the reaction device 715 for nucleic acid analysis. Moreover, the operation of injecting another reagent followed by detection is repeated multiple times, so that the data of nucleic acid samples can be read off. The nucleic acid analyzer is controlled by a computer, so that it can automatically perform the above operation.

Various forms of nucleic acid analysis can be conducted using the nucleic acid analyzer of the present invention, such as DNA sequencing and hybridization. In particular, DNA sequencing (DNA sequence determination) can be performed using the nucleic acid analyzer of the present invention. A method for DNA sequencing is not limited. DNA sequencing is preferably performed by Sequencing by Ligation. The sequencing by ligation to a technique that involves binding fluorescence-labeled probes in sequential order to single-stranded DNA as a template on a microparticle so as to determine a sequence of 2 bases at a time. With the use of the method, several tens to hundreds of by can be decoded per cycle, and data of several tens of Gb can be analyzed in a single run. In the sequencing by ligation, a fluorescence-labeled oligonucleotide is repeatedly hybridized, so that parallel sequencing can be performed. Such a sequencing method using sequencing by ligation can be performed according to Science 2005, vol. 309, pp. 1728-1732, for example.

Example 2

A nucleic acid analysis method using the nucleic acid analyzer of the present invention is as explained below. The analysis method was performed according to the method disclosed in Science 2005, vol. 309, pp. 1728-1732 (Non-patent Document 2).
(1) Library Construction A target nucleic acid sample was purified using a Dneasy Tissue kit (QIAGEN) and then the nucleic acid sample was fragmented. For DNA fragments, a tag sequence was added to both ends of a template DNA using an End-it DNA End Repair kit (EpiCentre). After purification of the template to which the tag sequence had been added, a spacer sequence was added to the template, and then it is treated with exonuclease, so that a template for RCA (Rolling Circle Amplification) was prepared. The thus obtained template was subjected to RCA using a random hexamer, so as to amplify the template. After purification of the amplification product with Microcon-30 (Millipore), the resultant was fragmented with a restriction enzyme. The thus fragmented products were subjected to gel purification, a tag library having a length of 70 bases was extracted. After ligation of a primer to the thus extracted tag library, PCR amplification was performed and thus a library was constructed.

(2) Emulsion PCR

A PCR solution, MyOne (Trademark) paramagnetic streptavidin magnetic beads (Dynal), and a library solution were added to an oil solution comprising light mineral oil (Sigma) and then emulsion PCR was performed. A solution containing a surfactant was added to the amplification solution, and then high-speed centrifugation was performed. Solvent substitution was performed using magnet and thus an aqueous bead solution containing DNA for measurement, that is, DNA having many amplification products, on the surface was prepared.

(3) Immobilization of Beads Having DNA on Their Surfaces on the Reaction Device for Nucleic Acid Analysis A primer with the phosphorylated 5' end was ligated to the beads with nucleic acid samples obtained in (2), so that a phosphate group as a functional group for immobilization was added to the ends of the nucleic acid samples on the beads. An aqueous solution of beads with nucleic acid samples (the 5' ends of which had been phosphorylated) was injected into the reaction device for nucleic acid analysis of the present invention comprising titania as a sample-immobilizing layer. Centrifugation was performed so that the surface having the sample-immobilizing layer was laterally-placed. The reaction device was retained at 40° C. for 12 hours, with the surface (having the immobilizing layer) positioned on the lower side, and thus beads with DNA were immobilized on titania.

(4) Forming of Blocking Layer

An aqueous sodium dodecyl sulfite solution was injected via a solution inlet port, and then maintained at 40° C. for 12 hours, so that a blocking layer was introduced on titania.

(5) Nucleic Acid Analysis

A reaction device for nucleic acid analysis, on which beads having nucleic acid samples on their surfaces had been immobilized, was installed in the nucleic acid analyzer 714 of the present invention. An aqueous solution containing an anchor primer was injected to the reaction device 715 for nucleic acid analysis via a nozzle 720. The aqueous solution within the reaction device 715 was heated to 60° C. using a holder unit 716 and then maintained at 42° C. After injection of an aqueous solution containing primers labeled with a dye for sequencing and a ligation enzyme, it was maintained at 35° C. for 30 minutes. Flow channels within the reaction device 715 were washed with buffer, and then labeled primers that had remained unreacted were removed. The reaction device 715 for nucleic acid analysis was transferred with a stage unit 717, and then exposed to excitation light with a detection unit 722, so that fluorescence introduced to beads with a plurality of nucleic acid samples within detection regions was detected. After repeating of a ligation reaction, washing, and fluorescence detection for multiple times, ligation products obtained with the use of the anchor primer and the labeled primer were degraded and removed using DNA uracilation and endonuclease. Through repeating of ligation reaction, washing, and detection using a new anchor primer, and further degradation and removal of ligation products followed by a series of detection using a new anchor primer, a DNA sequence was determined.

INDUSTRIAL APPLICABILITY

Various nucleic acid reactions can be conducted using the reaction device for nucleic acid analysis or the nucleic acid analyzer of the present invention. Furthermore, nucleic acid analysis such as DNA sequencing can be conducted.

EXPLANATION OF REFERENCE NUMERALS

101, 201, 301, 401, 501, 601: substrate
102, 202, 302, 402, 502, 602: sample-immobilizing layer 103, 203, 303, 403, 503, 603: nucleic acid sample
104, 304, 404, 504, 604: carrier
105, 205, 305, 405, 505, 605: blocking layer
506, 606: spacer
507, 607: second substrate
508: solution inlet port
509: solution outlet port
510: flow channel edge part
511: flow channel
612: mold film
613: hollow part
714: nucleic acid analyzer
715: reaction device for nucleic acid analysis
716: holder unit
717: stage unit
718: reagent container
719: solution delivering unit
720: nozzle
721: nozzle transport unit
722: detection unit
723: waste solution container All publications, patents, and patent applications cited herein are incorporated herein by reference in their entirety.

The invention claimed is:

1. A reaction device for nucleic acid analysis, comprising:
   a substrate,
   a sample-immobilizing layer on the substrate,
   a nucleic acid sample or a carrier having a nucleic acid sample on its surface, which is immobilized on the sample-immobilizing layer through phosphate group or phosphoester bond of the nucleic acid, and
   a blocking layer that covers an area other than an area where the nucleic acid sample or the carrier is bound to the sample-immobilizing layer, wherein the sample-immobilizing layer is formed of an inorganic oxide, the blocking layer is selected from the group consisting of a carboxylic compound, a sulfuric acid compound, a salt thereof, and a mixture of at least 2 types of these compounds, the compound used for the formation of the blocking layer has a hydrophobic site, the hydrophobic site is long chain alkyl group, a carboxylic acid group and/or sulfate group within the compound binds to the inorganic oxide, and the inorganic oxide is selected from the group consisting of titania, zirconia, alumina, zeolite, vanadium pentoxide, silica, sapphire, tungsten oxide, tantalum pentoxide, and a mixture of at least 2 types thereof.

2. The reaction device for nucleic acid analysis according to claim 1, comprising:
   a first substrate that comprises the sample-immobilizing layer, a nucleic acid sample or a carrier having a nucleic acid sample on its surface, which is immobilized on the sample-immobilizing layer through phosphate group or phosphoester bond of the nucleic acid, and
   a blocking layer that covers an area other than an area where the nucleic acid sample or the carrier is bound to the sample-immobilizing layer, wherein the sample-immobilizing layer is formed of an inorganic oxide;
   a second substrate; and
   a spacer having a hollow part for formation of a flow channel, wherein
   the first substrate and the second substrate are adhered to each other via the spacer to form the flow channel between the substrates,
   within the flow channel, the sample-immobilizing layer, the nucleic acid sample or the carrier having the nucleic acid sample on its surface, which is immobilized on the immobilizing layer, and the blocking layer that covers an area other than an area where the nucleic acid sample or the carrier is bound to the sample-immobilizing layer are present, and
   a solution inlet port and a solution outlet port that are in communication with the flow channel are provided.

3. The reaction device for nucleic acid analysis according to claim 2, wherein the spacer has a thickness of 1 mm or less.

* * * * *